United States Patent [19]

Imura et al.

[11] Patent Number: 5,569,490
[45] Date of Patent: Oct. 29, 1996

[54] TETRACALCIUM PHOSPHATE-BASED MATERIALS AND PROCESSES FOR THEIR PREPARATION

[75] Inventors: Akitoshi Imura, Sakai; Toru Saito, Takatsuki; Shiro Ikegami, Ibaragi, all of Japan

[73] Assignee: Osaka Cement Co., Ltd., Osaka, Japan

[21] Appl. No.: 458,713

[22] Filed: Jun. 2, 1995

Related U.S. Application Data

[62] Division of Ser. No. 360,330, Dec. 21, 1994, which is a division of Ser. No. 74,154, Jun. 9, 1993, Pat. No. 5,409,982, which is a division of Ser. No. 728,683, Jul. 12, 1991, abandoned.

[30] Foreign Application Priority Data

Jul. 27, 1990 [JP] Japan ................... 2-200071
Sep. 28, 1990 [JP] Japan ................... 2-262903

[51] Int. Cl.⁶ ........................................................ B05D 7/00
[52] U.S. Cl. ..................... 427/212; 427/399; 423/305; 423/308; 264/125
[58] Field of Search ........................ 427/399, 212; 423/305, 308; 264/125

[56] References Cited

U.S. PATENT DOCUMENTS

| | | | |
|---|---|---|---|
| 4,097,935 | 7/1978 | Jarcho | 3/1.9 |
| 4,207,306 | 6/1980 | Jarcho | 423/633 |
| 4,518,430 | 5/1985 | Brown et al. | 106/35 |
| 4,636,526 | 1/1987 | Dorman et al. | 521/61 |
| 4,684,673 | 8/1987 | Adachi | 523/116 |
| 4,698,375 | 10/1987 | Dorman et al. | 523/115 |
| 4,836,994 | 6/1989 | Inoue et al. | 423/308 |
| 4,861,733 | 8/1989 | White | 501/1 |
| 4,990,163 | 2/1991 | Ducheyne et al. | 623/66 |
| 5,035,711 | 7/1991 | Aoki et al. | 623/11 |
| 5,053,212 | 10/1991 | Constantz et al. | 423/305 |
| 5,077,079 | 12/1991 | Kawamura et al. | 427/2 |
| 5,135,396 | 8/1992 | Kuboki | 433/228.1 |
| 5,180,426 | 1/1993 | Sumita | 106/35 |
| 5,223,029 | 6/1993 | Oonishi et al. | 106/35 |
| 5,238,491 | 8/1993 | Sugihara et al. | 106/35 |
| 5,342,441 | 8/1994 | Mandai et al. | 106/35 |

*Primary Examiner*—Shrive Beck
*Assistant Examiner*—David M. Maiorana
*Attorney, Agent, or Firm*—Larson & Taylor

[57] ABSTRACT

The invention provides (i) a process for preparing tetracalcium phosphate particles, the process comprising the steps of (1) sintering or fusing a powder mixture at a temperature of not lower than 1,400° C., the mixture comprising a powder of calcium source and a powder of phosphorus source in a Ca/P molar ratio of 2/1, and about 0.005 to about 5 parts of an aluminum compound, calculated as $Al_2O_3$, per 100 parts of tetracalcium phosphate to be produced in terms of the theoretical amount, and (2) finely dividing the obtained product; (ii) tetracalcium phosphate particles prepared by said process; (iii) apatite-coated tetracalcium phosphate particles; (iv) a process for preparing the apatite-coated tetracalcium phosphate particles; (v) a tetracalcium phosphate-based setting composition; (vi) a composition for forming a hardening material using coated tetracalcium phosphate particles and an acidic aqueous solution; and (vii) the composition as defined in (vi) in which the acidic aqueous solution can satisfy the concentration relationships as represented below:

(a) 25% ≦ citric acid ≦ 50%

(b) 30% ≦ citric acid+phosphoric acid ≦ 70%

(c) 10% ≦ citric acid−phosphoric acid ≦ 50%

10 Claims, 8 Drawing Sheets

TETRACALCIUM PHOSPHATE-BASED MATERIALS AND PROCESSES FOR THEIR PREPARATION

This is a division of application Ser. No. 08/360,330 filed Dec. 21, 1994 which in turn is a division of 08/074,154, filed Jun. 9, 1993 now U.S. Pat. No. 5,409,982 which in turn is a division of 07/728,683 filed Jul. 12, 1991 (now abandoned).

INDUSTRIAL FIELD OF THE INVENTION

The present invention relates to tetracalcium phosphate particles useful as osteosynthetic materials, dental materials and the like, and to processes for preparing the same.

The present invention also concerns with tetracalcium phosphate particles coated with a material, such as apatite, having an affinity for the living body, processes for preparing the same, and compositions for producing cured materials or products which contain such tetracalcium phosphate particles.

The term "fused state" used herein refers to a state in which the starting particles have been fluidized as a whole by heating. The term "sintered state" used herein denotes a state in which the starting particles have not been fluidized by heating but have apparently disappeared to form a homogeneous phase. The term "porous state" used herein means a state in which the starting particles have reacted one another on heating, but are present substantially as they are without complete change of original configuration.

The parts and the percentages used herein are all by weight unless otherwise specified.

PRIOR ART

Tetracalcium phosphate ($Ca_4(PO_4)_2O$) is a phosphoric acid compound which is the main inorganic component of bones, teeth and so on. Tetracalcium phosphate has a high chemical activity and reacts at room temperature with an aqueous solution of, e.g. inorganic acid, saturated or unsaturated organic acid or a homopolymer or a copolymer of unsaturated organic acid, or a physiological saline or the like to undergo setting. The obtained hardened material or product has an affinity for the living body and is useful as an osteosynthetic material, a dental material and so on. 10 In preparation of tetracalcium phosphate, $CaCO_3$, $CaO$, $Ca(OH)_2$ or the like has been used as a Ca source, $P_2O_5$, $H_3PO_4$, $NH_4H_2PO_4$, $(NH_4)_2HPO_4$ or the like as a P source, and $CaHPO_4$, $Ca(H_2PO_4)_2$ or the like as a Ca and P sources. Tetracalcium phosphate can be prepared by Various processes depending on the kinds of the materials used. Most predominantly employed is a dry process as shown below in which a mixture of $CaCO_3$ and $CaHPO_4$ is calcined:

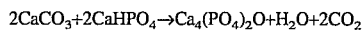

$$2CaCO_3 + 2CaHPO_4 \rightarrow Ca_4(PO_4)_2O + H_2O + 2CO_2$$

This process requires calcination of a mixture of the starting particles at a temperature of about 1,300 to about 1,600° C. and rapidly cooling of the obtained product to about 400° C. (at a cooling rate of not lower than about 10° C./min), and gives a product of phosphoric acid compounds containing a predominant amount of tetracalcium phosphate. When the mixture is calcined at not lower than 1,600° C. in this process, the obtained product is composed of a phase mixture of a porous portion and a semi-fused portion, posing the problem that the obtained product (tetracalcium phosphate) has an irregular quality. Furthermore, the tetracalcium phosphate produced by calcination even at about 1,300° to about 1,600° C. is highly reactive and very unstable, so that the product being cooled at a low cooling rate is caused to absorb water vapor in the atmosphere at 1,200° to 400° C., readily producing hydroxyapatite. With these problems, the process necessitates rigid control of calcining temperature, moisture content in the atmosphere within the calciner during cooling and cooling rate in order to obtain a tetracalcium phosphate of stable quality in a higher yield.

However, it is difficult to remove the moisture in the atmosphere within the calciner from the viewpoint of practical operation. Forced cooling of the product in the calciner is technically difficult and causes damage to refractory materials of calciner wall due to rapid cooling.

Given below are proposed processes for preparing a setting composition containing tetracalcium phosphate particles for use as osteosynthetic materials, osteosynthetic fillers, dental cement and so on:

(1) a process comprising admixing tetracalcium phosphate particles with an aqueous solution of TCA cycle-type organic acid;

(2) a process comprising admixing tetracalcium phosphate particles with an aqueous solution which is similar in composition to a tissue fluid in the living body, such as a physiological saline, a phosphate buffer or the like;

(3) a process comprising admixing tetracalcium phosphate particles with an aqueous solution of polysaccharide;

(4) a process comprising admixing tetracalcium phosphate particles with an aqueous solution of a homopolymer or a copolymer of unsaturated organic acid; and (5) a process comprising conducting a suitable combination of above processes (1) to (4).

These setting compositions are provided to clinicians in the form of a powder-liquid pack product comprising a combination of powder and liquid materials. In treatment, clinicians must knead the powder and liquid materials to obtain a paste or a clay-like mixture for use in any desired form. Moreover, after application to the affected part, the composition must be rapidly set or cured and firmly fixed thereto to exhibit a high biological activity. Yet these requirements can not be fully met by the setting or curable compositions produced by any of the above processes (1) to (5). The tetracalcium phosphate, which is the main component of the powder material, has a high chemical activity and is alkaline. It rapidly undergoes setting reaction when mixed with an acidic aqueous solution and thus is difficult to make into a homogeneous composition which can retain a suitable softness for a specific period of time.

In view of these drawbacks, attempts have been made to assure a sufficient treating time and enhance the operational efficiency in treatment. For example, an acid concentration in the liquid material has been reduced or the water content of the composition has been increased to improve the properties of the composition to be set or to control the setting time. In respect of the powder material, attempts have been made to inhibit the setting reaction of tetracalcium phosphate to the greatest extent possible by admixing therewith apatite, tricalcium phosphate, calcium monohydrogenphosphate, citrate, alkali phosphate or the like. However, these attempts have resulted in considerable impairment of properties of tetracalcium phosphate-based setting composition, and have failed to enhance the properties for setting reaction sufficiently to make up for the impairment. In short, the attempts have provided no complete solution to the problem.

Tetracalcium phosphate particles have been tentatively mixed with a neutral or substantially neutral aqueous solution. The attempt, however, has markedly decreased the setting reaction rate, whereby the tetracalcium phosphate-based composition has become unlikely to exhibit the required mechanical and physical characteristics and has been made alkaline, causing the hazard of acting as an irritant in the living body.

For the foregoing reasons, tetracalcium phosphate, although suitable for use as medical materials, dental materials or the like, has not been industrially provided in the form of a setting or curable tetracalcium phosphate-based composition having satisfactory properties, because of difficulties in handling and inability to fully exhibit the desired properties.

Means for Solving the Problems

In view of the foregoing state of the art, the present inventors conducted extensive research and found the following. When the starting materials for use in preparation of tetracalcium phosphate as admixed with a specific amount of an aluminum compound are heated to a sintered state or to a fused state, the tetracalcium phosphate thus obtained can markedly alleviate or substantially obviate the prior art problems entailed in preparation of tetracalcium phosphate.

According to the present invention, there are provided:
(i) a process for preparing tetracalcium phosphate particles, the process comprising the steps of (1) sintering or fusing a composition at a temperature of not lower than 1,400° C., the composition comprising a powder of calcium source and a powder of phosphorus source in a Ca/P molar ratio of 2/1, and about 0.005 to about 5 parts of an aluminum compound, calculated as $Al_2O_3$, per 100 parts of tetracalcium phosphate to be produced in terms of the theoretical amount, and (2) finely dividing the obtained product; and
(ii) tetracalcium phosphate particles prepared by the process as defined above in (i).

What are stated in (i) and (ii) will be hereinafter referred to as "first invention".

The present inventors' further research found the following. When the surface of tetracalcium phosphate particles is coated with apatite, the coated particles have the combined properties of the two materials, and can markedly mitigate or substantially overcome the prior art problems. In addition, a setting composition prepared from the obtained tetracalcium phosphate particles coated with apatite is equivalent or superior in properties to conventional setting compositions.

According to the invention, there are further provided:
(i) tetracalcium phosphate particles coated with apatite;
(ii) a process for preparing tetracalcium phosphate particles coated with apatite, the process comprising subjecting tetracalcium phosphate particles to hydration reaction; and
(iii) a tetracalcium phosphate-based setting composition comprising 100 parts by weight of the tetracalcium phosphate particles as defined above in (i) and about 5 to about 80 parts by weight of an aqueous solution of an acid, calculated as an acid.

What are stated above in (i), (ii) and (iii) will be hereinafter referred to as "second invention".

The present inventors' additional research revealed the following. An acidic aqueous solution predominantly containing citric acid and phosphoric acid is kneaded with a powder mixture predominantly containing tetracalcium phosphate particles having a double structure (the term "double structure" used herein refers to a structure wherein the tetracalcium phosphate particles are coated with apatite or like substance which is harmless to the living body or which has an affinity for the living body). The mixture can pronouncedly moderate or substantially solve the prior art problems.

In other words, according to the invention, there are also provided:
(i) a composition for forming a hardening material of high strength, the composition comprising 100 parts by weight of a powder mixture predominantly containing tetracalcium phosphate particles coated with a substance which is harmless to the living body and which has an affinity for the living body, and about 5 to about 80 parts by weight, calculated as an acid, of an acidic aqueous solution predominantly containing citric acid and phosphoric acid; and
(ii) a composition for forming a hardening material of high strength as defined above in (i) in which the acidic aqueous solution is able to satisfy all the concentration relations given below
   (a) $25\% \leq$ citric acid $\leq 50\%$
   (b) $30\% \leq$ citric acid+phosphoric acid $\leq 70\%$
   (c) $10\% \leq$ citric acid−phosphoric acid $\leq 50\%$.

What are stated above in (i) and (ii) will be hereinafter referred to as "third invention".

The first, second and third inventions will be described below in greater detail.

I. First Invention

The starting materials for preparation of tetracalcium phosphate according to the first invention may be the same as those used in the above-mentioned conventional processes. Yet when the obtained tetracalcium phosphate is used as a biological material, it is desirable to use acceptable food additives such as $CaHPO_4$, $CaHPO_4.2H_2O$, $CaCO_3$, $Ca_3(PO_4)_2$ and so on from the viewpoint of safety and the like. These additives are used in the form of particles usually having a particle size of up to 20 µm and an average particle size of about 5 µm.

Examples of aluminum compounds for use in preparation of tetracalcium phosphate are $Al_2O_3$, $Al(OH)_3$, $Al(PO_3)_3$, $AlPO_4$, $Al(H_2PO_4)_3$, $AlB_2$, $AlCl_3$, $AlF_3$, $AlI_3$, $Al_2(SiO_3)_3$, $Al_2(SO_4)_3$, $Al_2TiO_5$, etc. These compounds are usable singly or at least two of them can be used in mixture. Among the above examples, $Al_2O_3$ is desirable in view of the homogeneity of calcination product, control of calcining temperature and color of reaction product. The aluminum compound is used in the form of particles usually up to 20 µm in particle size and about 5 µm in average particle size. Alternatively $Al_2O_3$ may be partially replaced with a compound such as boron oxide ($B_2O_3$) in the IIIb group (to which Al pertains) in the short form of the periodic table.

The composition for use in the first invention comprises the Ca and P source materials in a Ca/P molar ratio of 2/1, and the aluminum compound in an amount of about 0.005 to about 5 parts in terms of $Al_2O_3$ per 100 parts of tetracalcium phosphate to be produced in terms of the theoretical amount. The mixture is calcined at not lower than 1,400° C. to a sintered or fused state, and left to stand for cooling in a calciner. The cooling rate may widely vary depending on the amount of starting materials used, the volume and structure of the calciner, and so on. In any case, the calcination product is cooled in the first invention at a lower rate than the rapid cooling conventionally done at a rate of not lower than 10° C./min. If before calcination, the mixture may be molded to an extent of not being collapsible, it eliminates the use of a container for the powder mixture, facilitates the handling, enables effective use of the volume of calciner interior, and hence is advantageous. A preferred amount of the aluminum compound is about 1 to about 2 parts per 100 parts of tetracalcium phosphate to be produced in terms of the theoretical amount. A preferred calcining temperature ranges from about 1,500° to about 1,550° C.

BRIEF DESCRIPTION OF THE DRAWINGS

FIG. 1 shows that the sintered state and the fused state can be widely varied according to the amount of $Al_2O_3$ used. For example, if the amount of $Al_2O_3$ used is 5%, a product in a sintered state can be obtained by calcining at about 1,450° C.

FIG. 2 indicates that the amount of $Al_2O_3$ exceeding 5% results in formation of apatite in excess amount, and therefore should be less than 5%.

Figure 1:
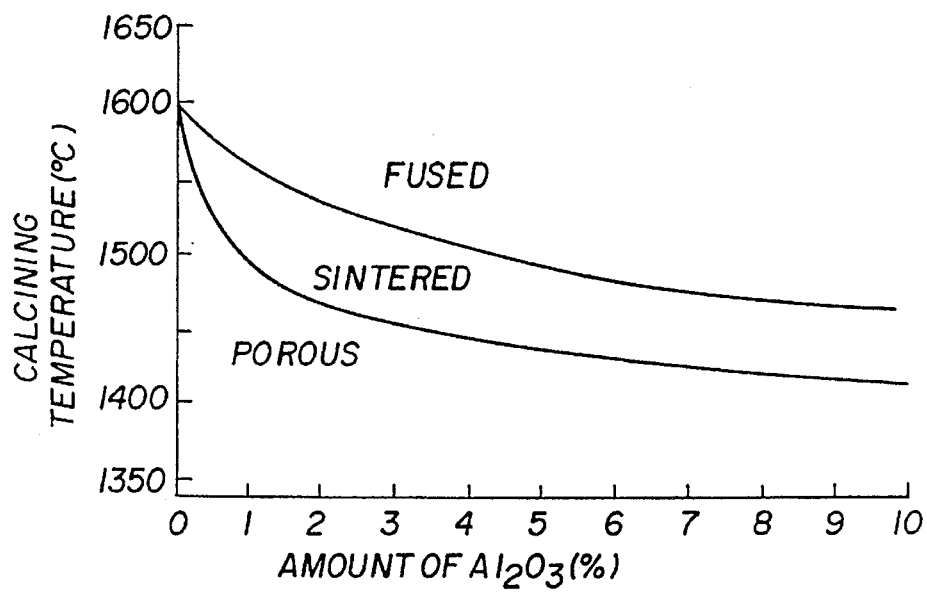
FIG. 1 shows a relationship between the amount of $Al_2O_3$ (per 100 parts of tetracalcium phosphate to be produced, calculated as the theoretical amount) relative to the amount of Ca and P source powders in a Ca/P molar ratio of 2/1, the calcining temperature and the sintered state or the fused state.
Figure 2:
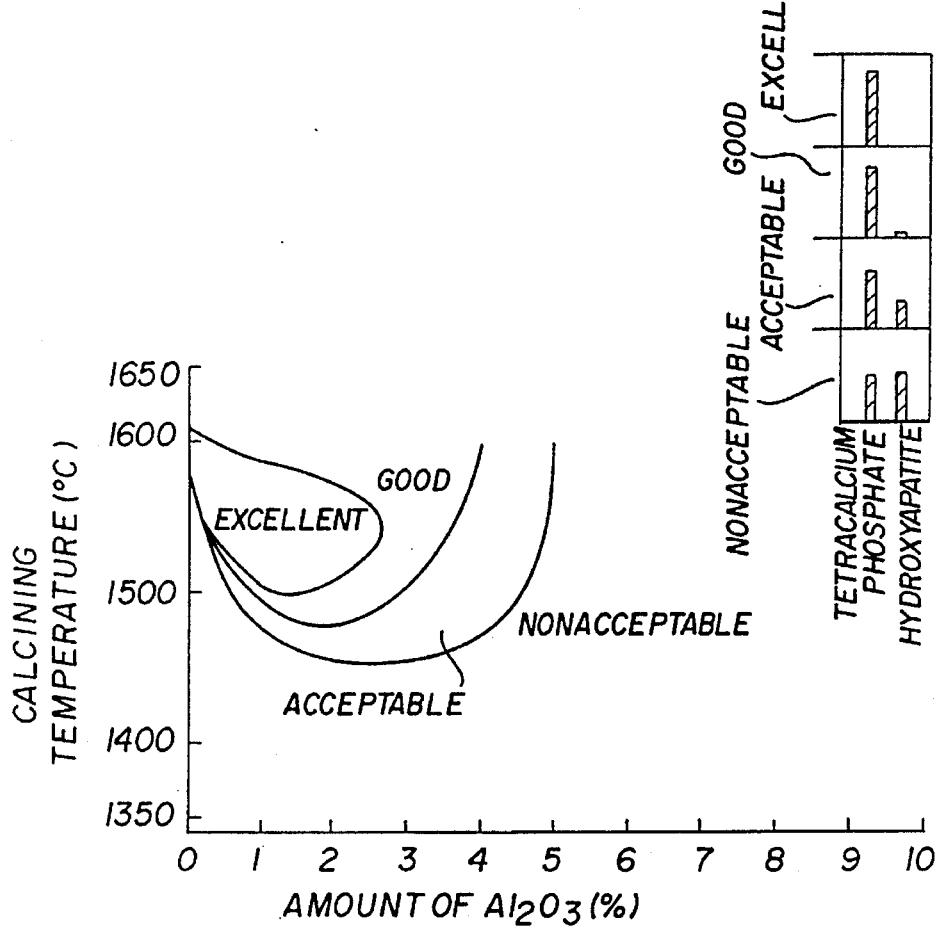
FIG. 2 graphically shows a relationship between the amount of $Al_2O_3$ (per 100 parts of tetracalcium phosphate to be produced calculated as the theoretical amount) relative to the amount of Ca and P source powders in a Ca/P molar ratio of 2/1, the calcining temperature and the proportion of the tetracalcium phosphate in the reaction product.

The tetracalcium phosphate obtained above is a product made hard by the calcining process, and contains little or no hydroxyapatite produced. The tetracalcium phosphate powders prepared by conventional calcining processes are usually ash-pale white and may be colored partially or wholly thickly dark or ash green due to the influence by a particular kind of materials used, small amounts of impurities, etc., whereby in most cases the value as a biological product is reduced from an aesthetic viewpoint. In contrast, the $Al_2O_3$-containing tetracalcium phosphate produced by the process of the first invention is uniformly pale blue or turquoise as a whole, namely aesthetically desirable free of the influence by a particular kind of materials used, small amounts of impurities, etc.

The properties of the tetracalcium phosphate prepared according to the first invention can be improved by addition of other additives. For example, tetracalcium phosphate is imparted radio-opacity or anti-fungus property by addition of at least one compound selected from alkaline earth metal compounds such as $BaSO_4$, $BaCO_3$, $SrSO_4$, $SrCO_3$, etc. and fluorine-containing compounds such as $BaSiF_6$, $SnF_2$, $CaF_2$, $NaF$, $AlF_3$, $Na_2SiF_6$, etc. These additives may be optionally employed to replace up to 60% of the aluminum compound calculated as $Al_2O_3$. These additives are used also in the form of particles usually up to 20 μm in particle size and about 5 μm in average particle size.

The hardening material of tetracalcium phosphate can be produced from the tetracalcium phosphate obtained in the first invention. Such hardening material can be prepared by mixing (A) a mixture of 100 parts of tetracalcium phosphate particles prepared by the process of the first invention and about 0.005 to about 50 parts of a silica-alumina based amorphous glass powder, and (B) about 30 to about 60%, based on the weight of the mixture, of a TCA cycle-type carboxylic acid or a polyacrylic acid represented by the formula (a)

wherein n is 1,000 to 100,000.

The tetracalcium phosphate particles for use in production of the hardening material are usually up to 20 μm in particle size and about 5 μm in average particle size.

Useful silica-alumina based glass powders include those prepared by melting and rapidly cooling a powder mixture comprising predominantly silica and alumina, and optionally, small amounts of calcium, fluorine, sodium, phosphorus, titanium, strontium and the like to obtain a vitreous product and pulverizing the product. When the amount of the silica-alumina based amorphous glass powder is less than 0.005 part per 100 parts of tetracalcium phosphate powder, the composition scarcely exhibits the effect expected to be produced by the addition thereof. On the other hand, if more than 50 parts of the glass powder is used, the cured product of the composition tends to show a scarcely improved or a decreased strength. It is preferred to use about 8 to about 15 parts of silica-alumina based amorphous glass powder per 100 parts of tetracalcium phosphate powder. The silica-alumina based amorphous glass powder usually has a particle size of up to 10 μm and about 3 μm on the average.

TCA cycle-type carboxylic acids for use in preparation of a hardening material include citric acid, malonic acid, malic acid, maleic acid, lactic acid, fumaric acid, ascorbic acid, succinic acid, gluconic acid, glutaric acid, pyruvic acid, etc. At least one of these acids and said polyacrylic acid is used in the form of an aqueous solution if so required. The amount of the TCA cycle-type carboxylic acid and/or polyacrylic acid is about 30 to about 60% of the combined weight of the tetracalcium phosphate powder and the silica-alumina based amorphous glass powder.

The thus obtained hardening material of tetracalcium phosphate has a greater bulk density in view of the great bulk density of tetracalcium phosphate powder than conventional hardening materials, hence a high compressive resistance. Therefore the hardening materials thus produced are useful as osteosynthetic materials, dental materials and like biological materials.

II. Second Invention

The tetracalcium phosphate for use in the second invention is not specifically limited, e.g. to those prepared by specific processes. A preferred tetracalcium phosphate is one which contains apatite, calcium oxide or the like in the smallest amount possible. Such high-purity tetracalcium phosphate can be prepared as by a solid phase reaction method as represented below in which a $CaCO_3$ powder is admixed with a $CaHPO_4 \cdot 2H_2O$ powder and the mixture is calcined.

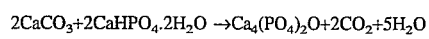

For preparation of tetracalcium phosphate particles coated with apatite according to the invention, tetracalcium phosphate is pulverized to a desired particle size. The particle size of the powder is not specifically limited but desirably about 20 μm or less and about 5 μm on the average, for use as the powder for a setting composition.

Next, the tetracalcium phosphate powder is subjected to hydration reaction. The hydration reaction proceeds merely by contact of the tetracalcium phosphate powder with water. Yet, to accelerate the reaction, the powder may be heated to a temperature of about 80° to about 100° C., preferably to about 95° C., or a reaction accelerator may be added. Useful reaction accelerators include organic acids such as citric acid, lactic acid, tartaric acid, succinic acid, etc.; salts thereof; inorganic acids such as hydrochloric acid, phosphoric acid, sulfuric acid, etc.; salts thereof; phosphate buffer solution and like pH adjusting agents for adjustment to neutrality or weak alkalinity; etc. These reaction accelerators are used in the form of an aqueous solution having a concentration of 1%. or less. In the hydration reaction, apatite coating is formed on the surface of tetracalcium phosphate particles by the reaction as illustrated below:

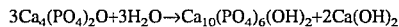
$3Ca_4(PO_4)_2O + 3H_2O \rightarrow Ca_{10}(PO_4)_6(OH)_2 + 2Ca(OH)_2$ Since apatite is highly stable in an alkaline aqueous solution, the water to be used in the reaction is preferably alkaline insofar as apatite coating can be formed. When the water to be used has a pH of 8 or less, octacalcium phosphate as well as apatite can be produced. Because octacalcium phosphate is a precursor of apatite, the coating is not necessarily formed of a high-purity apatite. For example, even if the coating is formed of a mixture of apatite and octacalcium phosphate or of a high-purity octacalcium phosphate, no practical problem would occur. In the above reaction, the calcium hydroxide is dissolved out in the water at the same time as the production of apatite, so that this eliminates the need to add a basic substance. Apatite coating can be satisfactorily produced even in an aqueous solution adjusted to alkalinity. On formation of apatite coating, the reaction rate is rapidly decreased, and the surface of particles would not be activated without addition of water or an aqueous solution of an acid. Therefore the quality of tetracalcium phosphate particles is not impaired due to the excessive progress of reaction.

The hydration reaction can be effectively conducted by other methods as listed below:
(a) by contact of tetracalcium phosphate with steam;
(b) by reaction at high temperatures utilizing the moisture in the atmosphere;
(c) by conducting a combination of the methods (a) and (b).

In the method (a), the treating time is substantially the same as in the treatment with water when the steam has a temperature of 100° C. or less. At a temperature of 100° C. or higher, the treating time is shortened as the temperature rises. For example, when steam of 300° C. is blended in air with tetracalcium phosphate powder, the treating time is 1 to 120 seconds, preferably about 30 to about 60 seconds.

The method (b) is carried out utilizing the characteristic of tetracalcium phosphate which can be converted into apatite by its positive absorption of moisture in the atmosphere at a temperature of about 300° to about 1,200° C. For, example, when air superheated to 500° C. is blended with tetracalcium phosphate powder, the treating time is about 1 to about 120 seconds, preferably about 30 to about 60 seconds.

In the method (c), the surface treatment is effected while controlling the partial pressure of steam and the temperature in the atmosphere. In other words, the method (c) is a combination of methods (a) and (b). For example, when air of 350° C. adjusted to a partial pressure of steam to 15 Torr is blended with tetracalcium phosphate powder, the treating time is about 1 to about 120 seconds, preferably about 30 to about 60 seconds.

A tetracalcium phosphate powder having a double structure can be effectively produced by the following methods without resort to hydration reaction.
a) a method in which ultrafine apatite is adsorbed and fixed on the surface of tetracalcium phosphate particles; and
b) a method in which apatite in a liquid form is adhered to (or deposited on) and fixed on the surface of the tetracalcium phosphate particles.

These methods have the advantage that coating materials are not limited to apatite. Usable, in other words, is any material which can be gradually dissolved in an acidic aqueous solution. For use as a biological material, it is desirable to use materials which are harmless to the living body (such as tricalcium phosphate, dicalcium phosphate dihydrate, etc.).

The tetracalcium phosphate-based setting composition according to the second invention can be prepared by admixing the tetracalcium phosphate particles coated with apatite in the above manner with an aqueous solution of organic acid in an amount of about 5 to about 80%, calculated as an acid, based on the weight of the tetracalcium phosphate particles. The tetracalcium phosphate particles coated with apatite preferably have a particle size of about 20 μm or less and about 5 μm on the average.

Examples of useful organic acids are:
(a) citric acid, tartaric acid, malonic acid, malic acid, maleic acid, lactic acid, succinic acid, fumaric acid, ascorbic acid, gluconic acid, glutaric acid, pyruvic acid and like TCA cycle-type carboxylic acids;
(b) phosphoric acid;
(c) homopolymers of acrylic acid represented by the formula

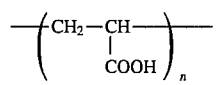

wherein n is 50 to 50,000;
(d) copolymers of acrylic acid and itaconic acid represented by the formula

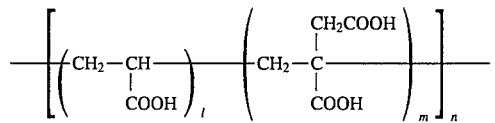

wherein l is 5 to 10, m is 1 to 5 and n is 50 to 50,000;
(e) copolymers of acrylic acid and fumaric acid represented by the formula

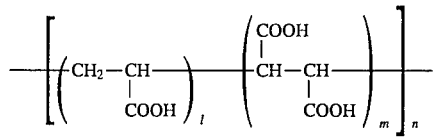

wherein l is 5 to 10, m is 1 to 5, and n is 50 to 50,000.

These acids are usable singly or at least two of them can be used in mixture. The acid is usually used in the form of an aqueous solution having the materials dissolved in pure water used as a solvent in a concentration of about 30 to about 70%.

The tetracalcium phosphate-based setting composition thus obtained can fully exhibit any of the inherent properties of tetracalcium phosphate not at an impaired level but an improved level unlike conventional setting compositions. Therefore these setting compositions are particularly useful as medical materials, dental materials and like biological materials. III. Third Invention The hardening material prepared by mixing the powder material and liquid material according to the third invention is equivalent or superior in properties to conventional biological materials, and also comparable or superior in physical and mechanical properties to hardening materials of known compositions having no affinity for the living body (such as zinc phosphate cement).

We discuss below in more detail the powder material and liquid material constituting the setting composition of the third invention and the process for preparing a hardening material.

A. Powder Material

The powder material for use in the third invention is tetracalcium phosphates particles coated with a material which is harmless to the living body and which has an affinity therefor.

A tetracalcium phosphate powder to be used can be prepared by any suitable process and is desirably a high-purity product (more preferably 98% or higher purity) having the lowest possible contents of apatite, calcium oxide and the like. Such high-purity tetracalcium phosphate can be prepared by a solid phase reaction method as illustrated below, as in the second invention, in which a mixture of $CaCO_3$ powder and $CaHPO_4 \cdot 2H_2O$ powder is calcined:

$2CaCO_3 + 2CaHPO_4 \cdot 2H_2O \rightarrow Ca_4(PO_4)_2O + 2CO_2 + 5H_2O$ In the solid phase reaction method, a tetracalcium phosphate of higher quality can be obtained by adding an alumina powder ($Al_2O_3$) to tetracalcium phosphate, and heating the mixture to a sintered state (Japanese Unexamined Patent Publication No.180705/1990).

A tetracalcium phosphate powder having a double structure which is used in the third invention can be produced as follows. First a tetracalcium phosphate is pulverized to a desired particle size and classified. The particle size of tetracalcium phosphate particles for use herein may be varied according to a particular utility of the setting composition and is not specifically limited. It is preferred to adjust tetracalcium phosphate particles to a particle size of about 20 μm or less and about 5 μm on the average.

Subsequently a coating material lower in chemical activity than tetracalcium phosphate is applied to the surface of the above-obtained tetracalcium phosphate particles to form a coating thereon. The coating material is not specifically limited provided that it is stable in storage and is able to gradually dissolve or to release from the surface of tetracalcium phosphate particles on contact with the liquid material to be described below. The coating material for use in preparing medical materials, dental materials, etc. is required to be harmless to the living body or to have an affinity therefor. The surface of tetracalcium phosphate particles can be coated by methods not specifically limited. When apatite coating having an affinity for the living body is formed, a liquid-solid phase hydration reaction as represented below is carried out to obtain tetracalcium phosphate particles having a double structure:

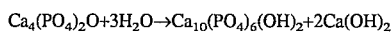
$Ca_4(PO_4)_2O + 3H_2O \rightarrow Ca_{10}(PO_4)_6(OH)_2 + 2Ca(OH)_2$ Apatite or hydroxyapatite which can be used in the invention include those having a chemical composition represented by the formula

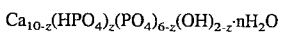
$Ca_{10-z}(HPO_4)_z(PO_4)_{6-z}(OH)_{2-z} \cdot nH_2O$ wherein n=0 to 2.5 and z=0 to 1.

Also useful are apatites other than hydroxyapatite such as fluorine-containing apatite having OH group substituted by fluorine, carboxyapatite having OH group substituted by carbonate, etc. which can produce the same level of effect. The term "apatite" used herein include these apatites.

The thickness of the apatite coating is not specifically limited, usually in the range of about 0.01 to about 1 μm.

B. Liquid Material

The liquid material for use in the third invention is an aqueous solution comprising citric acid and phosphoric acid which can satisfy all of the concentration relationships represented by:
(a) 25%≦citric acid≦50%
(b) 30%≦citric acid+phosphoric acid≦70%
(c) 10%≦citric acid−phosphoric acid≦50%

If citric acid or phosphoric acid is singly used, the desired result is not obtained, of course, in the invention. Even if these two acids are used, the desired setting compositions can not be obtained unless the concentration relationships as shown above in (a) to (c) are completely fulfilled. In the case of not fulfilling them, the obtained compositions can not give a hardening product having improved properties, or quickly set or are brought into sand-like or semi-dried clay-like state.

Given below are preferred concentration relationships of citric acid and phosphoric acid in the aqueous solution as the liquid material:
(d) 35%≦citric acid≦45%
(e) 35%≦citric acid+phosphoric acid≦60%
(f) 20%≦citric acid−phosphoric acid≦45%

The most preferred concentration relationships of citric acid and phosphoric acid in the aqueous solution are as follows:
(g) 37%≦citric acid≦42%
(h) 45%≦citric acid+phosphoric acid≦55%
(i) 23%≦citric acid−phosphoric acid≦42%
(j) 7%≦phosphoric acid≦15%

Insofar as citric acid and phosphoric acid in the aqueous solution can satisfy all of the concentration relationships (a) to (c), the solution may incorporate therein up to 10% of at least one of other organic acids or inorganic acids. Useful organic and inorganic acids are hydrochloric acid, nitric acid, ascorbic acid, polycarboxylic acid, etc.

Optionally malic acid and/or lactic acid can partially replace citric acid (up to 40%) although the use thereof slightly deteriorates the properties of cured product such as compressive strength, solubility in water, etc.

The phosphoric acid to be incorporated in the acidic aqueous solution is at least one acid selected from the group consisting of orthophosphoric acid, pyrophosphoric acid, polyphosphoric acid, metaphosphoric acid and phosphorus acid.

C. Process for Forming A Hardening Material

The setting composition according to the third invention can be prepared by admixing about 5 to about 80 parts, calculated as an acid, of the liquid material with 100 parts of the powder material immediately before use. The obtained setting composition is applied in the conventional manner to the affected part to be treated, as it is or, when required, as admixed with barium phosphate, calcium fluoride, X-ray contrast medium, other anti-fungus, medical materials, etc.

In this case, phosphoric acid is reacted with tetracalcium phosphate in the presence of citric acid, producing apatite and contributing to marked increase of strength. In conventional setting compositions, phosphoric acid is present as a substance which is detrimental to the living body, and has been considered a minor component of biological compositions from biological, physical and mechanical viewpoints. In contrast, phosphoric acid exhibits a unique action in the third invention.

According to the first invention, the following remarkable results can be obtained.

(1) Sintering or fusing of starting particles eliminates the needs for the rapid cooling and the dehumidification and drying in calciners as conventionally done.

Therefore tetracalcium phosphate can be obtained using a common calciner without use of a calciner of special structure, consequently at lower costs.

(2) Tetracalcium phosphate is prepared in a high yield with a high purity.

(3) A Ca source and a P source powders are not fused by calcination at lower than 1,600° C. although depending on the purity of compounds used. On the other hand, use of $Al_2O_3$ according to the first invention enables sintering and fusing at pronouncedly reduced temperatures. Hence the first invention is advantageous in terms of energy.

(4) The incorporation of $Al_2O_3$ enables calcination at a temperature in a wider range, so that the calcination can notably reduces the variability of products from lot to lot and the irregularity of composition in products, whereby products of stably uniform quality can be obtained.

(5) While calcination of only a Ca source and P source compounds gives aesthetically inferior products, calcination thereof in the first invention can provide products of uniformly pale blue to turquoise color or aesthetically excellent properties because of incorporation of $Al_2O_3$.

(6) Hardening materials obtained using tetracalcium phosphate according to the first invention have a great bulk density and a high shatter resistance.

According to the second invention, the following remarkable results can be produced.

(1) Apatite coating can be formed on the surface of tetracalcium phosphate particles by means of simple procedure without need for special apparatus.

(2) The tetracalcium phosphate particles coated with apatite remain stable in quality for an extended period and excellent in resistance to weathering and in storage properties.

(3) The apatite-coated tetracalcium phosphate particles have improved mechanical and physical properties while retaining the properties of tetracalcium phosphate as biological materials.

(4) Setting compositions having various setting properties can be obtained by adjusting the conditions for surface treatment and thus can be used for an extended range of applications of tetracalcium phosphate as biological materials.

According to the third invention, the following remarkable results can be achieved.

(1) The finally obtained cured or hardened product is given pronouncedly enhanced mechanical and physical properties (compressive strength, curing time, film thickness, etc.) without being impaired in the excellent properties of tetracalcium phosphate as biological materials.

(2) The obtained setting composition gives hardened products equivalent or superior in mechanical and physical properties to those formed from conventional biologically inactive setting compositions (such as zinc phosphate cement).

(3) The obtained setting composition provides a hardening material of high strength, and thus are usable for a wider range of applications as biological materials.

(4) Phosphoric acid which has found a narrow range of utility as biological materials in conventional materials specifically improves the properties of setting compositions due to the synergistic effect produced by conjoint use with citric acid.

(5) The obtained setting composition is set after a suitable period (neither too long nor too short), thereby facilitating the operation.

(6) The hardened product has a suitable hardness which leads to enhancement of operational efficiency.

Examples

Given below are Examples and Comparison Examples to clarify the features of the invention in further detail.

Example 1

Powdery $CaCO_3$ and $CaHPO_4$ having an average particle size of about 5 μm were mixed together in a molar ratio of 1: 1. $Al_2O_3$ was added in an amount of 0.1% based on the weight of the mixture. The resulting mixture was calcined in a furnace in the atmosphere at 1600° C. for 2 hours for sintering. The sintered body was allowed to stand for cooling in the furnace and withdrawn therefrom when the sintered body was cooled to 400° C.

Figure 3:
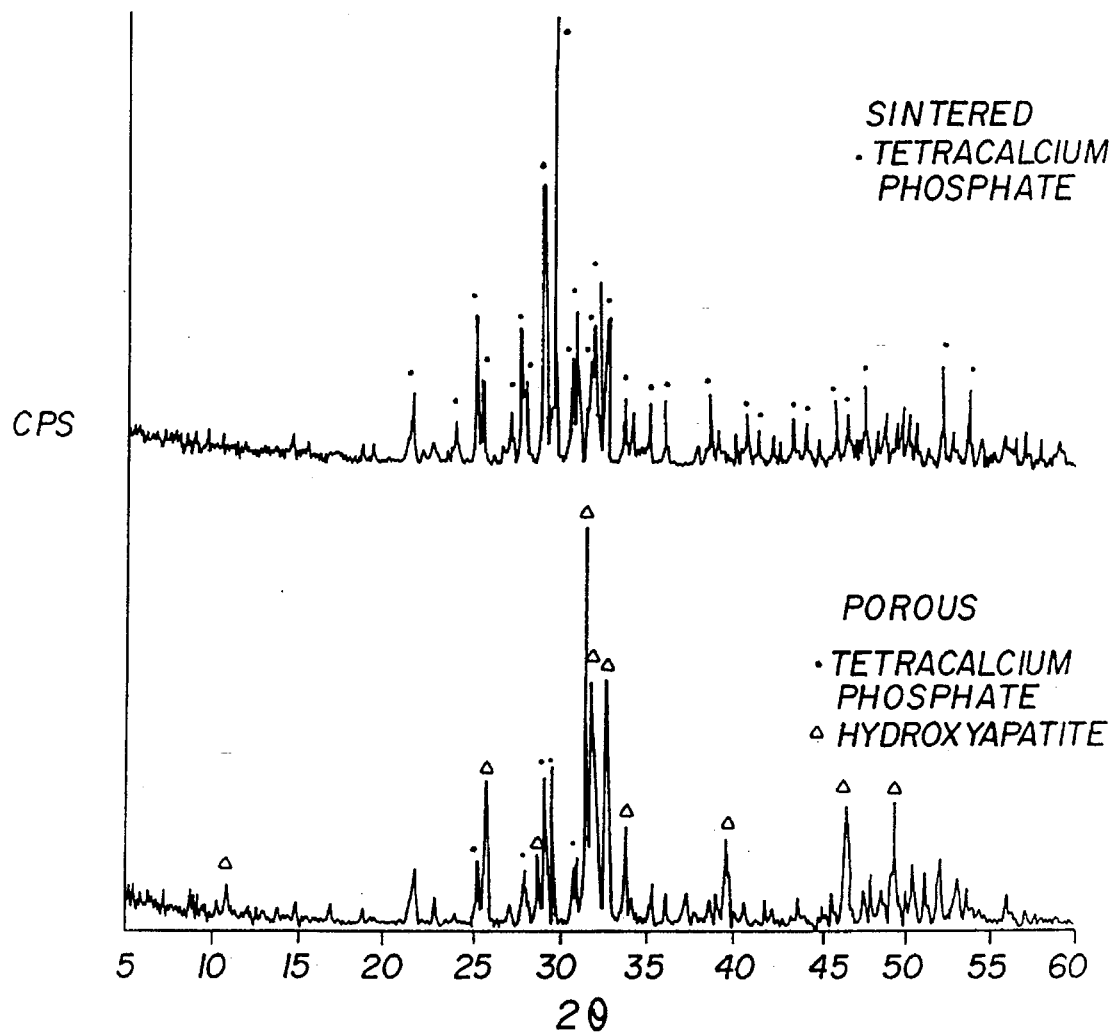
FIG. 3 shows x-ray diffraction scans of the products of Example 1 and of Comparative Example 1.

FIG. 3 shows, in the upper position, the results of X-ray diffractometry using the sintered body obtained.

The results shown in FIG. 3 reveal that the product substantially consists of tetracalcium phosphate alone.

Comparison Example 1

The same procedure as in Example 1 was repeated except that the mixture was calcined at 1500° C. The product obtained was porous.

The product was subjected to X-ray diffractometry with the results shown in the lower position in FIG. 3.

The results indicated in FIG. 3 clearly show that the product contains a large quantity of hydroxyapatite in addition to tetracalcium phosphate.

Example 2

The same procedure as in Example 1 was repeated except that the amount of $Al_2O_3$ was adjusted to the range of 0.005 to 50% and that the mixture was calcined at 1350° to 1600° C.

Figure 4:
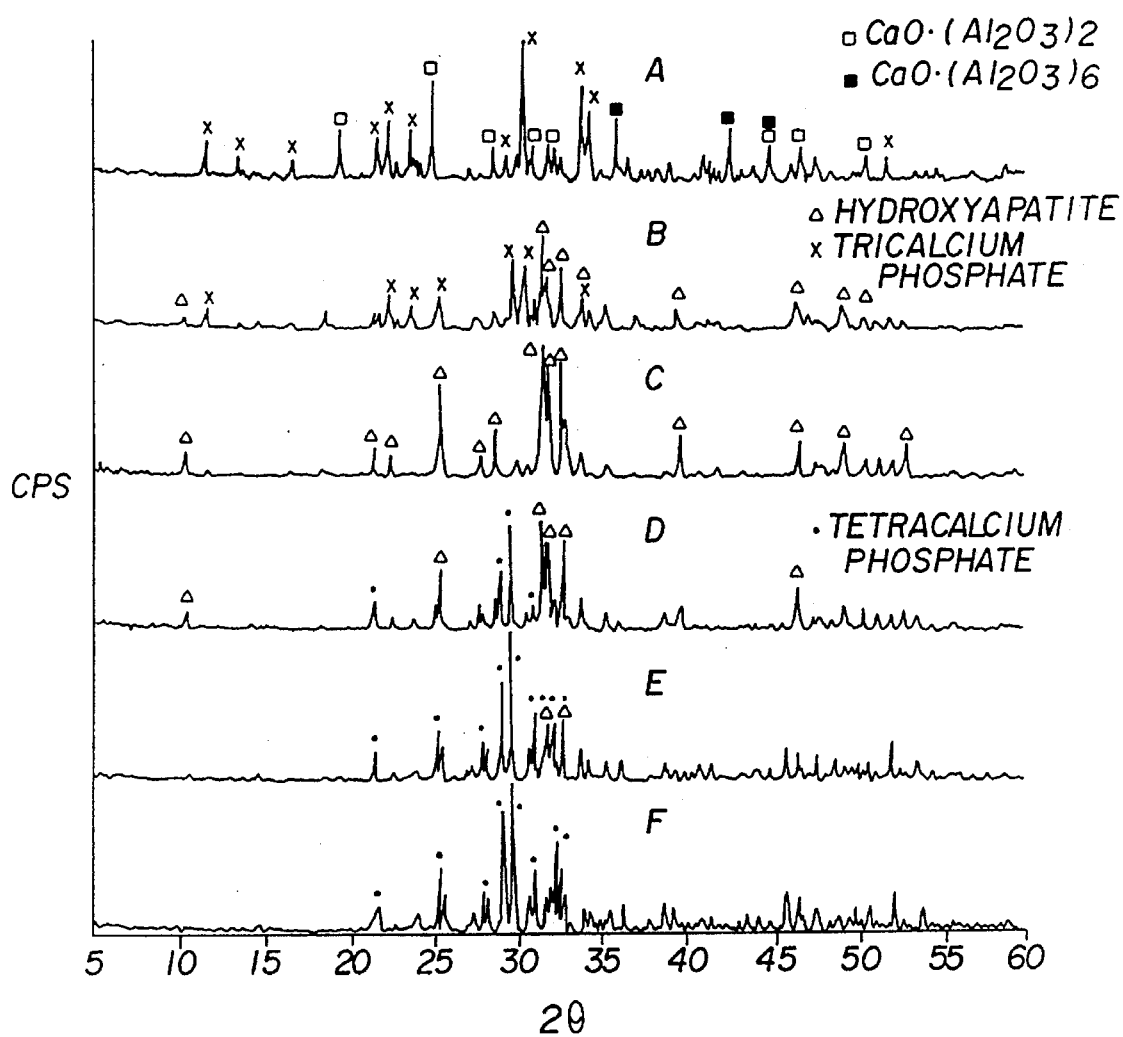
FIG. 4 is an x-ray diffraction scan of the product of Example 2.

The product was subjected to X-ray diffractometry with the results shown by the symbols A to F in FIG. 4.

The relationship between the results A to F in FIG. 4 on one hand and the amount of $Al_2O_3$ added and the calcining temperature on the other hand is as follows.

I. FIG. 4-A $Al_2O_3$: 50%

Calcining temperature: 1350° C.

II. FIG. 4-B $Al_2O_3$: 20%

Calcining temperature: 1400° C.

III. FIG. 4-C $Al_2O3$: 10%

Calcining temperature: 1450° C.

IV. FIG. 4-D $Al_2O_3$: 5%
Calcining temperature: 1450° C.
V. FIG. 4-E
$Al_2O_3$: 1.5%
Calcining temperature: 1500° C.
VI. FIG. 4-F
$Al_2O_3$: 0.005%
Calcining temperature: 1600° C.

The results A to F shown in FIG. 4 reveal that if the amount of $Al_2O_3$ is 5% or lower, the melting temperature markedly decreases, whereby tetracalcium phosphate can be satisfactorily produced. However, even when $Al_2O_3$ is added in an amount of more than 5%, the melting temperature does not markedly decrease and the production of tetracalcium phosphate is inhibited. For this reason, the upper limit of $Al_2O_3$ amount to be added is 5%.

Reference Example 1

To 100 parts of powdery tetracalcium phosphate (average particle size: 5 μm) obtained in Example 2 (the amount of $Al_2O_3$ added: 1.5%) was added 10, 30 or 50 parts of silica-alumina based powdery glass (silica: 50%, alumina: 30% and the total amounts of minor components such as Sr, Ti, Ca and the like: 20%). To 100 parts of the resulting powdery mixture was added 50 parts (calculated as an acid) of an aqueous solution containing 45% of citric acid, 45% of malic acid or 30% of malic acid and 15% of polyacrylic acid (n=about 16000 in the foregoing formula (a)), giving a hardened product.

For comparison, a hardened product was obtained in the same manner as above with the exception of using a conventional powdery tetracalcium phosphate which does not contain $Al_2O_3$.

Twenty four hours after the formation of cured product, each product was tested for compressive resistance (kgf/cm$^2$) with the results shown below in Table 1.

In Table 1, each symbol indicates the following.
A: silica-alumina based powdery glass was used in an amount of 10 parts
B: silica-alumina based powdery glass was used in an amount of 30 parts
C: silica-alumina based powdery glass was used in an amount of 50 parts
D: citric acid
E: malic acid
F: malic acid+polyacrylic acid

TABLE 1

|  | Acid | | |
| --- | --- | --- | --- |
|  | D | E | F |
| Conventional products |  |  |  |
| A | 653 | 810 | 803 |
| B | 621 | 773 | 781 |
| C | 580 | 751 | 766 |
| Reference Example |  |  |  |
| A | 1035 | 1260 | 1124 |
| B | 833 | 978 | 1031 |
| C | 720 | 880 | 893 |

The compressive resistance of the hardened product obtained with use of tetracalcium phosphate according to the present invention is about 1.5 times that of the hardened product obtained in the same manner using the conventional tetracalcium phosphate.

Example 3

Powdery CaO and $P_2O_5$ having a particle size of about 5 μm were mixed together in a molar ratio of 4:1, Further, powdery $Al_2O_3$ was added thereto in an amount of 0.5% based on the theoretical amount of the tetracalcium phosphate to be produced. The resulting mixture was calcined in a furnace in the atmosphere at 1550° C. for 2 hours for sintering. The sintered body was allowed to stand for cooling in the furnace. When the sintered body was cooled to 400° C., it was withdrawn from the furnace.

Figure 5:
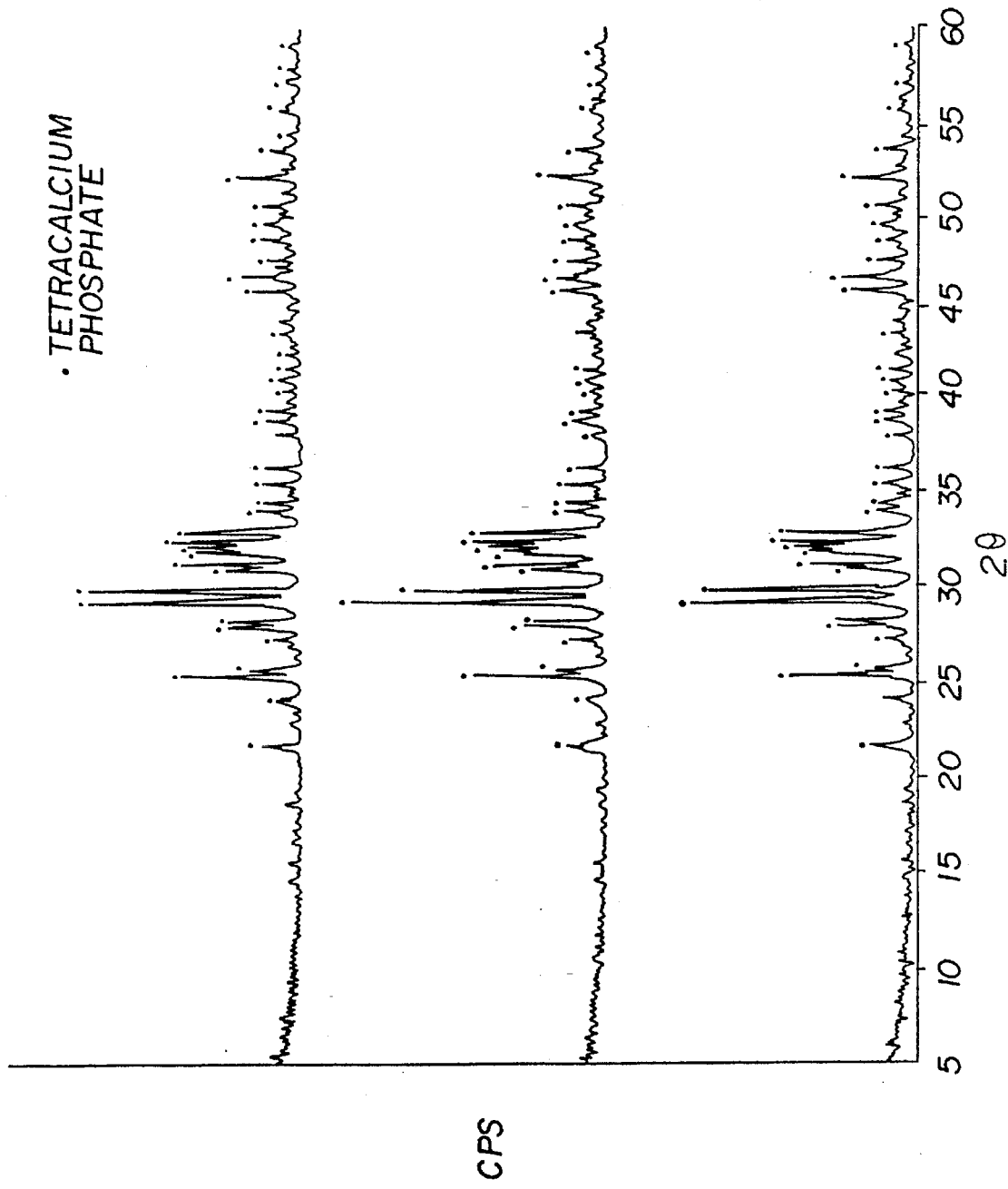
FIG. 5 is an x-ray diffraction scan of the product of Example 3.

The sintered body was subjected to X-ray diffractometry with the results shown in the upper position in FIG. 5.

Example 4

Powdery $Ca(OH)_2$ and $Ca(H_2PO_4)_2$ having a particle size of about 5 μm were mixed together in a molar ratio of 3:1. Powdery $Al_2O_3$ was added thereto in an amount of 1% based on the theoretical amount of tetracalcium phosphate to be produced. The resulting mixture was calcined in a furnace in the atmosphere at 1500° C. for 2 hours for sintering. The sintered body was allowed to stand for cooling in the furnace. When the sintered body was cooled to 400° C., it was withdrawn from the furnace.

The product obtained was subjected to X-ray diffractometry with the results shown in the intermediate position in FIG. 5.

Example 5

Powdery CaO and $(NH_4)H_2PO_4$ having a particle size of about 5 μm were mixed together in a molar ratio of 2:1. Powdery $Al_2O_3$ was added in an amount of 2% based on the theoretical amount of tetracalcium phosphate to be produced. The resulting mixture was calcined in a furnace in the atmosphere at 1500° C. for 2 hours for sintering. The sintered body was allowed to stand for cooling in the furnace and withdrawn when the sintered body was cooled to 400° C.

The product obtained was subjected to X-ray diffractometry with the results shown in the lower position in FIG. 5.

Reference Example 2

Powdery $CaCO_3$ and $CaHPO_4 \cdot 2H_2O$ having an average particle size of about 5 μm were mixed together in a Ca/P molar ratio of 2:1. The mixture was shaped and calcined in the atmosphere at 1600° C. for 3 hours to obtain a sintered body. The sintered body was pulverized into particles having the maximum particle size of up to 20 μm and an average particle size of about 5 μm, giving powdery tetracalcium phosphate.

Figure 6:
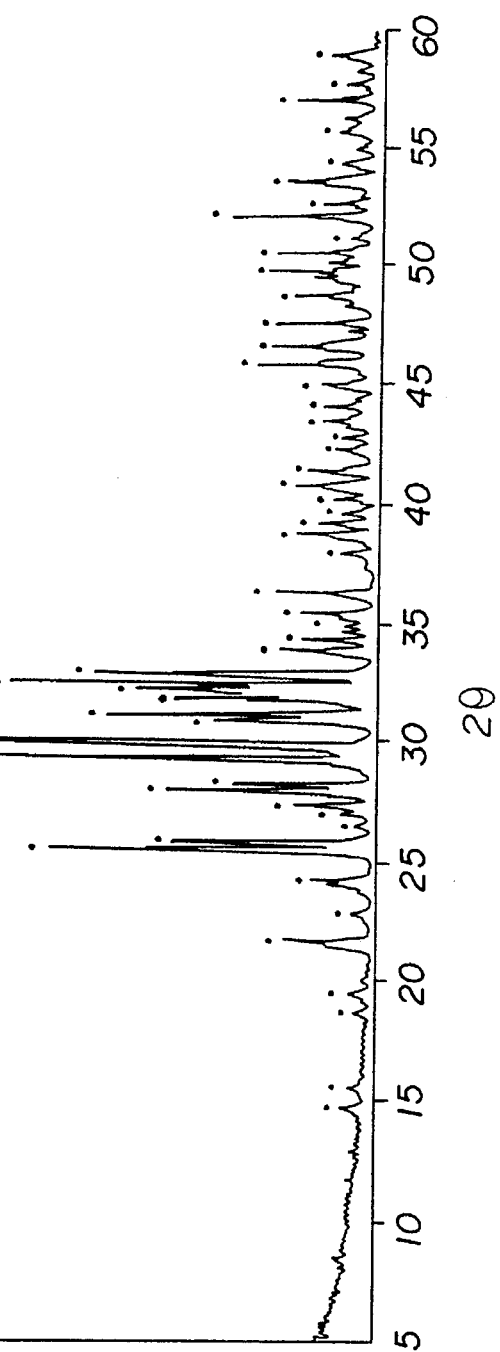
FIG. 6 is an x-ray diffraction scan of the product of Reference Example 2.

The product obtained was subjected to X-ray diffractometry with the results shown in FIG. 6. The results of Table 6 show that the product obtained is a high-purity one substantially consisting of tetracalcium phosphate alone.

In the following examples, the high-purity tetracalcium phosphate thus obtained was used.

Example 6

A 20 g quantity of purified water heated to 95° C. was added to 10 g of powdery tetracalcium phosphate. The resulting mixture was separated into seven portions to provide seven hermetically sealed samples. The samples were cured in a constant-temperature bath maintained at 95° C. and withdrawn therefrom 1 hour, 3 hours, 24 hours, 7 days, 14 days, 30 days and 60 days after the initiation of the curing, respectively. Each sample was dried at 105° C. and the particles obtained were subjected to X-ray diffractometry. The results are shown with symbols A to G in FIG. 7.

Figure 7:
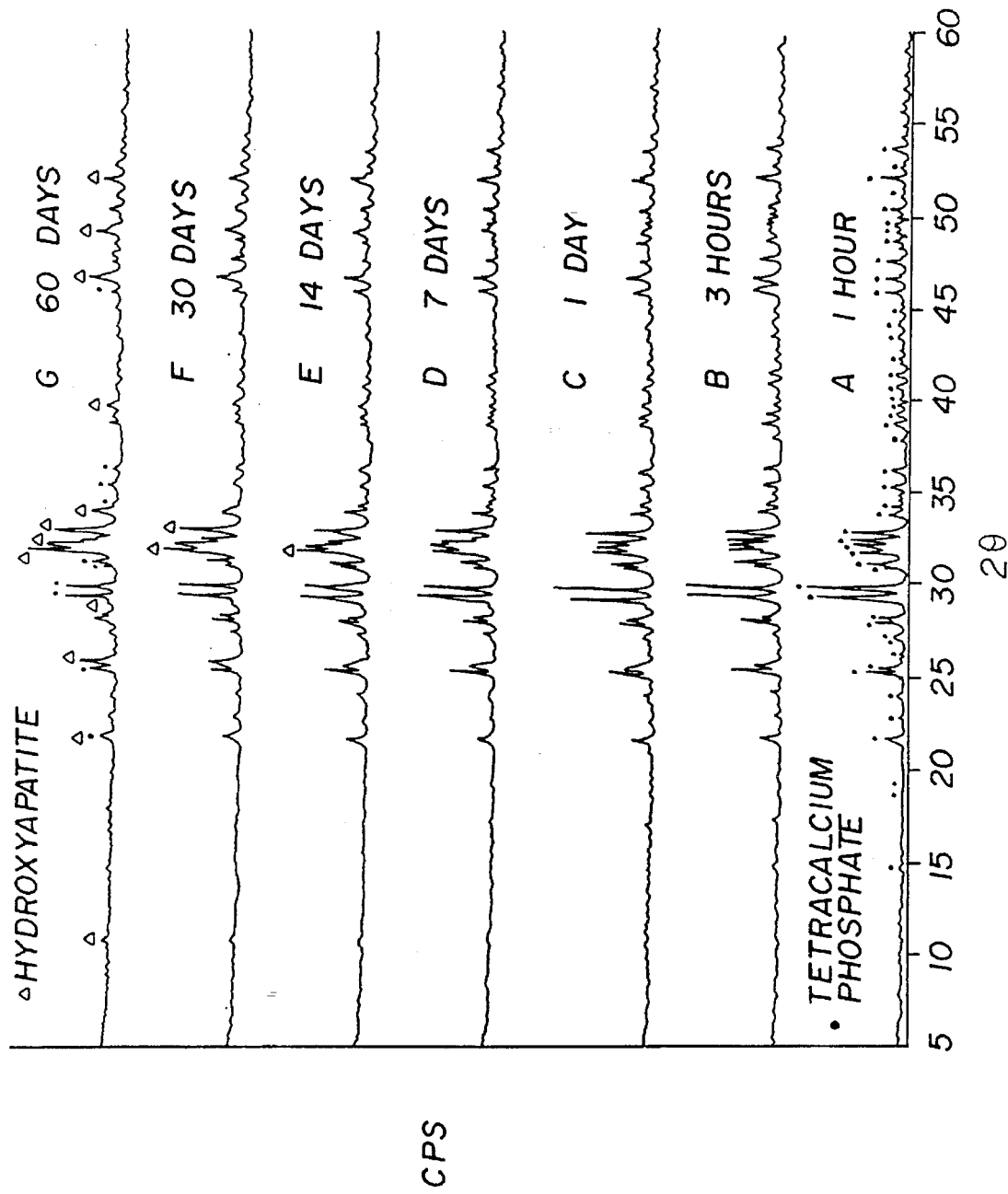
FIG. 7 is an x-ray diffraction scan of the product of Example 6.

The results A to G in FIG. 7 indicate that the tetracalcium phosphate was gradually transformed into hydroxyapatite and that the tetracalcium phosphate remained present even in hot water relatively stably for a prolonged period of time.

Example 7

A 2 g quantity of powdery tetracalcium phosphate was dispersed in 1 l of purified water and heated at 37° C. and 95° C. for 5 hours, respectively. The powder was separated by filtration and was dried by standing for 24 hours. The obtained particles were subjected to X-ray diffractometry.

Figure 8:
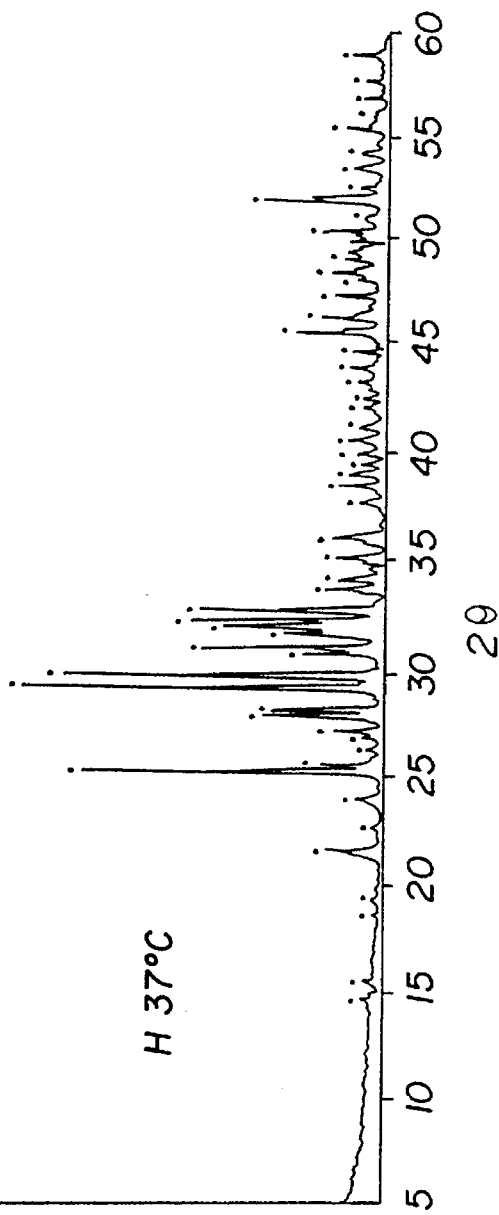
FIG. 8 is an x-ray diffraction scan of the product of Example 7.

The results of the X-ray diffraction are indicated at H and I in FIG. 8.

The results of FIG. 8 show that the tetracalcium phosphate obtained according to the present invention can be stably present in an excessive quantity of water.

Example 8

A 20 g quantity of purified water was added to 10 g of powdery tetracalcium phosphate. The resulting mixture was subjected to surface treatment under the conditions (temperature and time) as shown in Table 2 and separated by filtration. The cake was allowed to stand for drying for 24 hours, giving powder for setting composition. In Table 2, the FIGS. 1 to 40 designate the sample numbers. Thereafter an aqueous solution of citric acid at a concentration of 40% was mixed with the above powder to give setting compositions. The setting time of each composition was determined. The powder was mixed with the aqueous solution in a powder to liquid ratio of 2.3 g/ml. Table 3 shows the results.

TABLE 2

| Treatment Time | Treatment temperature | | | |
|---|---|---|---|---|
| | 23° C. | 37° C. | 50° C. | 95° C. |
| 1 min | 1 | 11 | 21 | 31 |
| 5 min | 2 | 12 | 22 | 32 |
| 10 min | 3 | 13 | 23 | 33 |
| 30 min | 4 | 14 | 24 | 34 |
| 1 hr | 5 | 15 | 25 | 35 |
| 3 hrs | 6 | 16 | 26 | 36 |
| 6 hrs | 7 | 17 | 27 | 37 |
| 12 hrs | 8 | 18 | 28 | 38 |
| 24 hrs | 9 | 19 | 29 | 39 |
| 72 hrs | 10 | 20 | 30 | 40 |

TABLE 3

| Sample No. | Setting time |
|---|---|
| 1 | Within 20 sec |
| 2 | Within 20 sec |
| 3 | Within 20 sec |
| 4 | Within 20 sec |
| 5 | 30 sec |
| 6 | 1 min |
| 7 | 4 min 30 sec |
| 8 | 4 min 45 sec |
| 9 | 6 min 15 sec |
| 10 | 7 min 50 sec |
| 11 | Within 20 sec |
| 12 | 40 sec |
| 13 | 1 min 50 sec |
| 14 | 3 min 45 sec |
| 15 | 4 min 30 sec |
| 16 | 4 min 55 sec |
| 17 | 5 min 10 sec |
| 18 | 5 min 30 sec |
| 19 | 6 min 45 sec |
| 20 | 7 min 40 sec |
| 21 | Within 20 sec |
| 22 | 30 sec |
| 23 | 45 sec |
| 24 | 2 min |
| 25 | 4 min |
| 26 | 4 min 20 sec |
| 27 | 4 min 30 sec |
| 28 | 4 min 40 sec |
| 29 | 6 min |
| 30 | 7 min 40 sec |
| 31 | 1 min 30 sec |
| 32 | 2 min |
| 33 | 4 min 45 sec |
| 34 | 5 min 30 sec |
| 35 | 5 min 40 sec |
| 36 | 5 min 45 sec |
| 37 | 5 min 50 sec |
| 38 | 6 min |
| 39 | 7 min 45 sec |
| 40 | 11 min 15 sec |

Example 9

A 100 g quantity of powdery tetracalcium phosphate was stirred for 3 hours in 200 g of distilled water heated to 95° C. and the resulting mixture was subjected to filtration. The cake was dried at 105° C. for 24 hours. The obtained powdery tetracalcium phosphate coated with apatite was mixed with aqueous solutions under the following conditions, giving setting compositions:, (a) the powder was mixed with. an aqueous solution of 40% citric acid in a ratio of the powder/liquid=2.4 (g/ml);

(b) the powder was mixed with an aqueous solution containing 40% citric acid and 5% polyacrylic acid in a ratio of powder/liquid=2.2 (g/ml);

(c) the powder was mixed with an aqueous solution of 38% citric acid, 1% tartaric acid and 2.5% polyacrylic acid in a ratio of powder/liquid=2.2 (g/ml);

(d) the powder was mixed with an aqueous solution of 29% citric acid, 10% malonic acid and 2.5% polyacrylic acid in a ratio of powder/liquid=2.3 (g/ml); and (e) the powder was mixed with an aqueous solution of 40% citric acid and 20% phosphoric acid in a ratio of powder/liquid=2.0 (g/ml).

The setting compositions thus obtained were tested for (1) setting time, (2) compressive strength after 24 hours (kgf/cm$^2$) and (3) film thickness, all by the test methods according to JIS T6602.

Table 4 shows the results.

TABLE 4

| Mixing conditions | (1) | (2) | (3) |
|---|---|---|---|
| (a) | 6 min 30 sec | 984 | 24 μm |
| (b) | 6 min 30 sec | 1239 | 29 μm |
| (c) | 5 min 30 sec | 1019 | 38 μm |
| (d) | 5 min 30 sec | 1123 | 25 μm |
| (e) | 4 min 45 sec | 1472 | 41 μm |

Comparison Example 2

Setting compositions were prepared in the same manner as in Example 9 with the exception of using tetracalcium phosphate particles not surface treated.

Setting compositions were tested by the same methods as in Example 9 with the results shown below in Table 5. In Table 5, the symbols (a) to (e) and (1) to (3) have the same meaning as in Table 4.

TABLE 5

| Mixing conditions | (1) | (2) | (3) |
|---|---|---|---|
| (a) | Within 30 sec | Impossible to measure | Impossible to measure |
| (b) | Within 30 sec | Impossible to measure | Impossible to measure |
| (c) | Within 30 sec | Impossible to measure | Impossible to measure |
| (d) | Within 30 sec | Impossible to measure | Impossible to measure |
| (e) | Within 30 sec | Impossible to measure | Impossible to measure |

As clear from the results shown in Table 5, the compositions prepared under the same mixing conditions as in Example 9 are set within a very short period of time, i.e. are set substantially instantaneously, thus failing to obtain a soft setting composition which is easy to handle.

Comparison Example 3

Setting compositions were produced under the same mixing conditions as in Example 9 except that tetracalcium phosphate not surface treated were used and that an increased amount of the acidic aqueous solution was used to obtain setting compositions having physical properties which can be measured.

The mixing Conditions (f) to (j) in Table 6 are as follows.

(f) the aqueous solution (a) in Example 9 was mixed in a ratio of powder/liquid=1.5 (g/ml)

(g) the aqueous solution (b) in Example 9 was mixed in a ratio of powder/liquid=1.5 (g/ml)

(h) the aqueous solution (c) in Example 9 was mixed in a ratio of powder/liquid=1.5 (g/ml)

(i) the aqueous solution (d) in Example 9 was mixed in a ratio of powder/liquid=1.5 (g/ml)

(j) the aqueous solution (e) in Example 9 was mixed in a ratio of powder/liquid=1.5 (g/ml)

Table 6 shows the results.

TABLE 6

| Mixing conditions | (1) | (2) | (3) |
|---|---|---|---|
| (f) | 4 min | 593 | 46 μm |
| (g) | 3 min 50 sec | 612 | 52 μm |
| (h) | 3 min 05 sec | 623 | 73 μm |
| (i) | 2 min 40 sec | 671 | 107 μm |
| (j) | 1 min 55 sec | 819 | 113 μm |

Example 10

Used as a powder material was a powdery tetracalcium phosphate (having a maximum particle size of 20 μm and an average particle size of 5 μm) having a double structure wherein the surface of particles was coated with apatite by subjecting the tetracalcium phosphate to hydration reaction. Used as a liquid material was an acidic aqueous solution containing citric acid and phosphoric acid. Using these materials, a setting composition sample was obtained by mixing the powder material and the liquid material in a ratio of powder/liquid=2.4 g/ml.

The concentrations of citric acid and phosphoric acid in the liquid material used for preparing the samples were as follows.

No. 41—citric acid=35%, orthophosphoric acid=7%

No. 42—citric acid=40%, orthophosphoric acid=5%

No. 43—citric acid=45%, orthophosphoric acid=5%

No. 44—citric acid=40%, orthophosphoric acid=10%

No. 45—citric acid=35%, orthophosphorlc acid=15%

No. 46—citric acid=40%, orthophosphorlc acid=15%

No. 47—citric acid=45%, orthophosphoric acid=15%

The setting compositions thus obtained were tested for (1) setting time, (2) compressive resistance (kgf/cm$^2$) after 24 hours and (3) film thickness, all by the test methods according to JIS T 6602.

Table 7 shows the results.

TABLE 7

|  | (1) | (2) | (3) |
|---|---|---|---|
| No. 41 | 6 min 10 sec | 1130 | 20 μm |
| No. 42 | 5 min 50 sec | 1231 | 21 μm |
| No. 43 | 4 min 45 sec | 1339 | 27 μm |
| No. 44 | 5 min 20 sec | 1828 | 22 μm |
| No. 45 | 5 min 10 sec | 1243 | 30 μm |
| No. 46 | 4 min 50 sec | 1619 | 24 μm |
| No. 47 | 4 min 5 sec | 1283 | 23 μm |

Example 11

Used as a powder material was a mixture of a 100-part of the same apatite-coated, double-structured tetracalcium phosphate particles as in Example 10, 25 parts of barium sulfate (X-ray contrast medium) and 2.5 parts of calcium fluoride (anti-fungus agent). The powder material was mixed with an acidic aqueous solution containing citric acid and phosphoric acid as a liquid material, giving a setting composition sample.

Given below are the concentrations of citric acid and phosphoric acid in the liquid material, and the ratio of the powdery/liquid employed for preparation of samples.

No. 48—citric acid=42% orthophosphoric acid=10% ratio of powder/liquid=2.5 g/ml

No. 49—citric acid=41% orthophosphoric acid=11% ratio of powder/liquid=2.6 g/ml

No. 50—citric acid=38%, orthophosphoric acid=8% ratio of powder/liquid=2.7 g/ml

The setting compositions thus obtained were tested for (1) setting time, (2) compressive resistance (kgf/cm$^2$) after 24 hours and (3) film thickness in the same manner as in Example 10.

Table 10 shows the results.

TABLE 8

|  | (1) | (2) | (3) |
| --- | --- | --- | --- |
| No. 48 | 4 min 30 sec | 1654 | 30 μm |
| No. 49 | 4 min 40 sec | 1792 | 29 μm |
| No. 50 | 4 min 20 sec | 1823 | 30 μm |

As clear from the results of Tables 7 and 8, the setting time of the samples Nos. 41 to 50 is in an ideal range of 4 to 8 minutes and the film thickness is about 30 μm, which means that the samples are neither too hard nor too soft, hence are easy to handle.

Since the average compressive resistance of natural bones is about 1500 kgf/cm$^2$, evidently the products of the invention have a sufficient strength for use as their substitutes.

Comparison Example 4

The same apatite-coated, double-structured powdery tetracalcium phosphate as used in Example 10 as a powder material was mixed with an acidic aqueous solution as a liquid material containing citric acid and phosphoric acid, giving a setting composition sample.

The concentrations of citric acid and phosphoric acid in the liquid material and the ratio of powder material to liquid material for preparation of samples were as follows.

No. 51—citric acid=51%, phosphoric acid=5% powder/liquid ratio=2.0 g/ml

No. 52—citric acid=46% phosphoric acid=26% powder/liquid ratio=2.0 g/ml

No. 53—citric acid=35% phosphoric acid=30% powder/liquid ratio=2.0 g/ml

No. 54—citric acid=30%, phosphoric acid=25% powder/liquid ratio=2.0 g/ml

No. 55—citric acid=24%, phosphoric acid=15% powder/liquid ratio=2.2 g/ml

No. 56—citric acid=23% phosphoric acid=7% powder/liquid ratio=2.2 g/ml

No. 57—phosphoric acid=10% powder/liquid ratio=2.4 g/ml

The setting compositions thus obtained were tested for (1) setting time, (2) compressive resistance after 24 hours (kgf/cm$^2$) and (3) film thickness in the same manner as in Example 10.

Table 9 shows the results.

TABLE 9

|  | (1) | (2) | (3) |
| --- | --- | --- | --- |
| No. 51 | Less than 30 seconds | Impossible to measure | Impossible to measure |
| No. 52 | Less than 30 seconds | Impossible to measure | Impossible to measure |
| No. 53 | Less than 30 seconds | Impossible to measure | Impossible to measure |
| No. 54 | Not set | Impossible to measure | Impossible to measure |
| No. 55 | Not set | Impossible to measure | Impossible to measure |
| No. 56 | Not set | Impossible to measure | Impossible to measure |
| No. 57 | Not set | Impossible to measure | Impossible to measure |

As clear from the results of Table 9, when the ratio of citric acid to phosphoric acid in a liquid material is outside the range specified in the invention, the obtained samples were set in an exceedingly short period of time, or were not cured, or were apparently set, but the hardened products exhibited a fatal defect of, e.g. having substantially no mechanical Strength, hence unsuited for use.

Comparison Examples 5 to 8

The following commercially available or known setting compositions for medical or dental use which consisted of powder material and liquid material were checked for physical properties in the same manner as in Example 10.

[Comparison Example 5]

Apatite-coated commercially available product A:

powder material: α-tricalcium phosphate liquid material: aqueous solution of organic high-molecular weight acid powder/liquid ratio=1.3 g/g

[Comparison Example 6]

Product disclosed in Japanese Unexamined Patent Publication No. 72363/1987:

powder material: tetracalcium phosphate liquid material: aqueous solution of citric acid powder/liquid ratio=2.0 g/g

[Comparison Example 7]

Product disclosed in Japanese Unexamined Patent Publication No. 176252/1989:

powder material: tetracalcium phosphate+dibasic calcium phosphate liquid material: aqueous solution of phosphoric acid powder/liquid ratio=3.8 g/g

[Comparison Example 8]

Product disclosed in Japanese Unexamined Patent Publication No. 100049/1989 powder material: α-tricalcium phosphate+tetracalcium phosphate liquid material: aqueous solution of a mixture of citric acid, saccharose and chitosan powder/liquid ratio=2.0 g/g The setting compositions thus obtained were tested for (1) setting time, (2) compressive resistance after 24 hours (kgf/cm$^2$) and (3) film thickness in the same manner as in Example 10.

TABLE 10

| Comp. Ex. | (1) | (2) | (3) |
| --- | --- | --- | --- |
| 5 | 6 min 10 sec | 541 | 20 μm |
| 6 | 2 min 50 sec | 910 | 57 μm |
| 7 | 35 min | 342 | 22 μm |
| 8 | 8 min 50 sec | 623 | 39 μm |

As clear from the results of Table 10, none of the obtained products had all of the following properties, namely an appropriate setting time (preferably about 2 to about 10 minutes), a compressive strength sufficient for use as substitutes for bones, teeth and the like (preferably kgf/cm$^2$ or higher), a softness which facilitates handling (preferably film thickness up to 30 μm) and like properties. In general, when any of the products was outstanding in a specific property, but poor in other properties.

Reference Example 3

Figure 9:
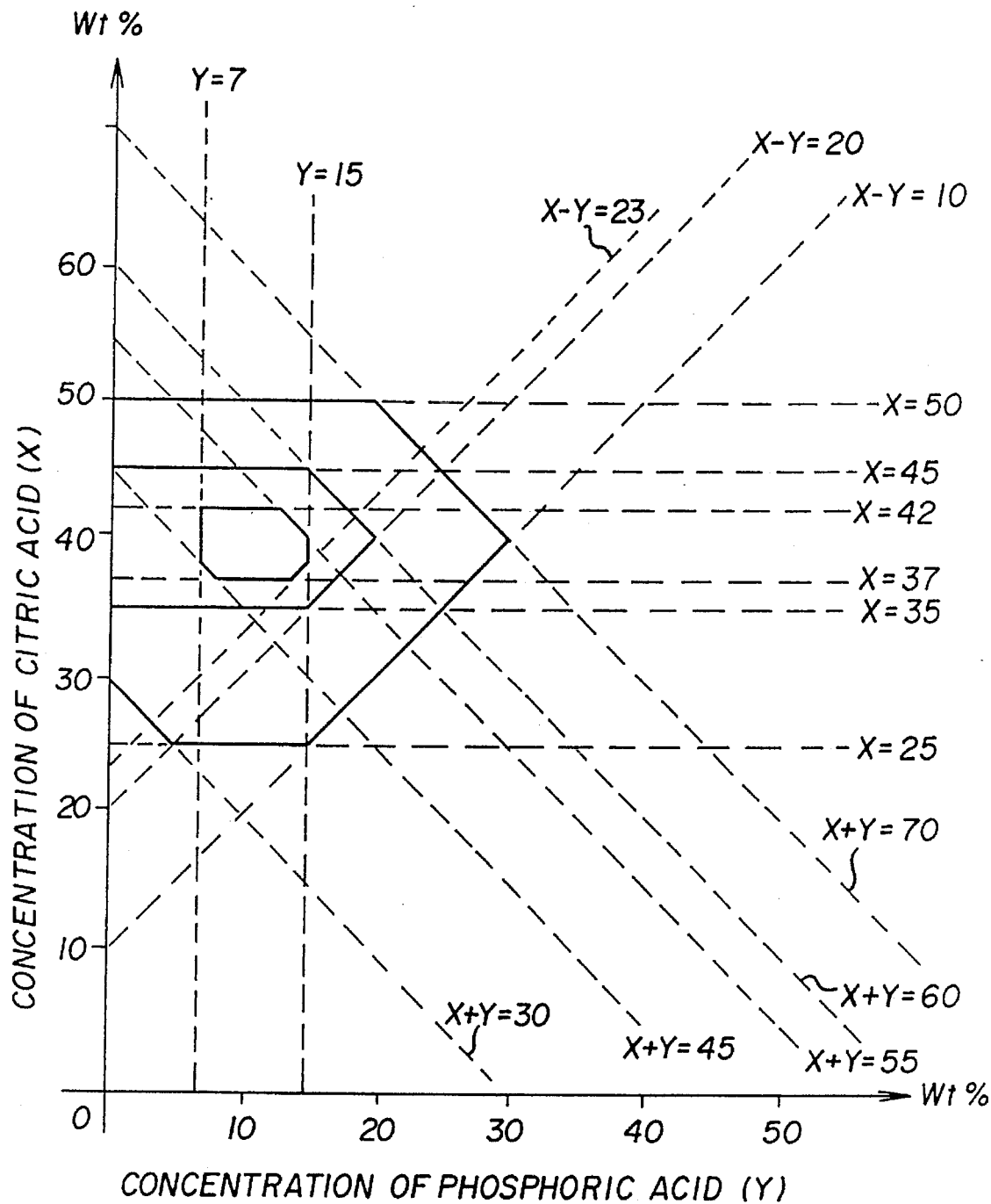
FIG. 9 is a graph showing the relationship in quantity between citric acid and phosphoric acid in the liquid material for setting compositions of the invention.

FIG. 9 graphically represents the relationships in quantity between citric acid and phosphoric acid in the liquid material for setting compositions of the invention, more specifically the relationship therebetween which results in improvement of properties (the range according to the invention), the relationship therebetween which results in increase of compressive strength (more preferred range according to the invention), and the relationship therebetween which results in highest degree of increase of compressive strength (most preferred range according to the invention).

The area surrounded by the outermost line indicates the ordinary range of the invention, the area surrounded by the intermediate line indicates the preferred range of the invention and the area surrounded by the innermost line indicates the most preferred range of the invention.

Example 12

The same procedure as in Example 10 was repeated with the exception of using citric acid and phosphoric acids in the following ratios, giving setting compositions wherein the ratio of powder/liquid was 2.4 g/ml.

No. 58—citric acid=40%, pyrophosphoric acid=10%
No. 59—citric acid=40%, polyphosphoric acid=10%
No. 60—citric acid=40%, metaphosphoric acid=10%
No. 61—citric acid=40%, phosphorous acid=10%

The setting compositions thus obtained were tested for (1) setting time, (2) compressive strength (kgf/cm$^2$) after 24 hours and (3) film thickness (μm), in the same manner as in Example 10.

Table 11 shows the results.

TABLE 11

|  | Setting time | Compressive strength | Thickness |
| --- | --- | --- | --- |
| No. 58 | 5 min 10 sec | 1750 | 25 |
| No. 59 | 5 min 15 sec | 1782 | 27 |
| No. 60 | 5 min 45 sec | 1611 | 28 |
| No. 61 | 6 min 10 sec | 1815 | 21 |

Example 13

Setting compositions were prepared in the same manner as in Example 10 except that citric acid and phosphoric acids were used in the following ratios and that the ratios of powder/liquid were as follows.

No. 62—citric acid=25% orthophosphoric acid=5% powder/liquid=3.0 g/ml
No. 63—citric acid=45% phosphorous acid=25% powder/liquid=1.0 g/ml
No. 64—citric acid=30% phosphorous acid=20% powder/liquid=2.2 g/ml
No. 65—citric acid=48%, orthophosphoric acid=5% powder/liquid=2.0 g/ml The setting compositions thus obtained were tested for (1) setting time, (2) compressive strength (kgf/cm$^2$) after 24 hours and (3) film thickness (μm), in the same manner as in Example 10.

TABLE 12

|  | Setting time | Compressive strength | Thickness |
| --- | --- | --- | --- |
| No. 62 | 7 min 30 sec | 1186 | 11 |
| No. 63 | 7 min 50 sec | 1027 | 12 |
| No. 64 | 6 min 15 sec | 1250 | 24 |
| No. 65 | 4 min 10 sec | 1247 | 26 |

Table 12 shows the results.

We claim:

1. A process for preparing tetracalcium phosphate particles, the process comprising the steps of (1) sintering or fusing a powder mixture at a temperature of not lower than 1,400° C., the mixture comprising a powder of calcium source and a powder of phosphorus source in a Ca/P molar ratio of 2:1, and about 0.005 to about 5 parts of an aluminum compound, calculated as $Al_2O_3$, per 100 parts of tetracalcium phosphate to be produced in terms of the theoretical amount, and (2) finely dividing the obtained product.

2. A process according to claim 1 wherein the calcium source and the phosphorus source are at least one member selected from the group consisting of $CaHPO_4$, $CaHPO_4 \cdot 2H_2O$ and $Ca_3(PO_4)_2$.

3. A process according to claim 1 wherein the calcium source is $CaCO_3$.

4. A process according to claim 1 wherein the particles of the calcium source, the phosphorous source and the aluminum compound have a particle size of up to 20 μm.

5. A process according to claim 1 wherein the particles of the calcium source, the phosphorous source and the aluminum compound have a particle size of about 5 μm on the average.

6. A process according to claim 1 wherein the aluminum compound is at least one member selected from the group consisting of $Al_2O_3$, $Al(OH)_3$, $Al(PO)_3$, $AlPO_4$, $Al(H_2PO_4)_3$, $AlB_2$, $AlCl_3$, $AlF_3$, $AlI_3$, $Al_2(SiO_3)_3$, $Al_2(SO_4)_3$ and $Al_2TiO_5$.

7. A process according to claim 1 wherein the amount of the aluminum compound is about 1 to about 2 parts, calculated as $Al_2O_3$, per 100 parts of tetracalcium phosphate to be produced in terms of the theoretical amount.

8. A process according to claim 1 wherein the calcining temperature is about 1,500° to about 1,550° C.

9. A process according to claim 1 wherein the aluminum compound, calculated as $Al_2O_3$, contains up to 60% of at least one member selected from the group consisting of $BaSO_4$, $BaCO_3$, $SrSO_4$, $SrCO_3$, $BaSiF_6$, $SnF_6$, $CaF_2$, $NaF$, $AlF_3$ and $Na_2SiF_6$.

10. Tetracalcium phosphate particles prepared by the process as defined in claim 1.

* * * * *